United States Patent [19]

Minowa et al.

[11] Patent Number: 5,190,952
[45] Date of Patent: Mar. 2, 1993

[54] 4-ACYLOXYQUINOLINE DERIVATIVES AND INSECTICIDAL OR ACARICIDAL COMPOSITIONS CONTAINING SAME

[75] Inventors: Nobuto Minowa; Tomoya Machinami; Seiji Shibahara; Keiichi Imamura; Michiaki Iwata; Masaru Shimura; Shigeharu Inouye, all of Yokohama, Japan

[73] Assignee: Meiji Seika Kabushiki Kaisha, Tokyo, Japan

[21] Appl. No.: 549,136

[22] Filed: Jul. 5, 1990

[30] Foreign Application Priority Data

Jul. 7, 1989 [JP] Japan ................. 1-176187

[51] Int. Cl.$^5$ ................. C07D 215/233; A01N 43/42; A01N 43/44
[52] U.S. Cl. ................. 514/297; 514/312; 546/79; 546/103; 546/153; 546/156
[58] Field of Search ................. 514/297.312, 290; 546/79, 103, 153, 156

[56] References Cited

U.S. PATENT DOCUMENTS 3,301,859  1/1967  Cheney et al. ................. 546/153

FOREIGN PATENT DOCUMENTS 374765  6/1990  European Pat. Off. ............. 546/153

OTHER PUBLICATIONS

Wells, J. Biol. Chem. 196 331-340, 1952.
Fleming et al. J. Chem. Soc (C), 1970 pp. 2426-2428.
Homma et al Soil Biology and Biochemistry 21(5) 1989 pp. 723 to 727.
Green, Protective Groups in Organic Chemistry (New York: J. Wiley and Sons, 1981), pp. 101-103.

Primary Examiner—Robert T. Bond
Assistant Examiner—E. C. Ward
Attorney, Agent, or Firm—Wenderoth, Lind & Ponack

[57] ABSTRACT

A 4-acyloxyquinoline derivative represented by the general formula (I):

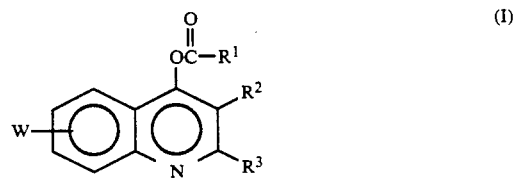

wherein $R^1$ represents a hydrogen atom, a $C_1$-$C_{18}$ alkyl, $C_2$-$C_{18}$ alkenyl, $C_3$-$C_{10}$ cycloalkyl which may be optionally substituted, phenylloweralkyl, phenoxyloweralkyl, aryl group, a group $OR^4$, where $R^4$ represents a lower alkyl or aryl group, or a group

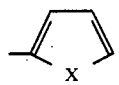

where X represents an oxygen or a sulphur atom; $R^2$ represents a hydrogen atom, a lower alkyl alkyl group or a group —$COOR^5$ where $R^5$ represents a hydrogen atom or a lower alkyl group; $R^3$ represents a hydrogen atom, a $C_1$-$C_{10}$ alkyl or $C_2$-$C_{10}$ alkenyl group, provided that $R^1$ does not represent $OR^4$ when $R^2$ is a hydrogen atom and $R^3$ is methyl; $R^2$ and $R^3$ together represent a group $(CH_2)_m$, wherein m is 3 or 4, and W represents a hydrogen atom, 1 to 4 halogen atoms, a lower alkyl or lower alkoxy group which may be the same or different and with which the left-hand nucleus is substituted, provided that the compound wherein $R^1$ represents methyl, $R^2$, $R^3$ and W each represent a hydrogen atom is excluded.

7 Claims, No Drawings

4-ACYLOXYQUINOLINE DERIVATIVES AND INSECTICIDAL OR ACARICIDAL COMPOSITIONS CONTAINING SAME

BACKGROUND

The present invention relates to a 4-acyloxyquinoline derivative and an insecticide containing it as an effective ingredient.

A variety of compounds having insecticidal or acaricidal activities have hitherto been developed. However, it is desired to develop a new insecticide having an excellent activity because of the problem such as the recent increase of insecticidal resistance.

SUMMARY OF THE INVENTION

It is an object of the present invention to provide novel compounds which have an excellent insecticidal and acaricidal activity.

Thus, the invention, in one aspect thereof, provides novel compounds having the formula (I):

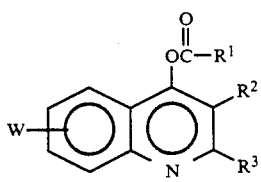

wherein $R^1$ represents a hydrogen atom, a $C_1-C_{18}$ alkyl, $C_2-C_{18}$ alkenyl, $C_3-C_{10}$ cycloalkyl which may be optionally substituted, phenylloweralkyl, phenoxyloweralkyl, aryl group, a group $OR^4$, where $R^4$ represents a lower alkyl or aryl group, or a group

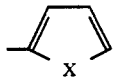

where X represents an oxygen or a sulphur atom; $R^2$ represents a hydrogen atom, a lower alkyl group or a group $—COOR^5$ where $R^5$ represents a hydrogen atom or a lower alkyl group; $R^3$ represents a hydrogen atom, a $C_1-C_{10}$ alkyl or a $C_2-C_{10}$ alkenyl group, provided that $R^1$ does not represent $OR^4$ when $R^2$ is a hydrogen atom and $R^3$ is methyl; $R^2$ and $R^3$ together represent a group $-(CH_2)_{\overline{m}}$, wherein m is 3 or 4, and W represents a hydrogen atom, 1 to 4 halogen atoms, a lower alkyl or lower alkoxy group which may be the same or different and with which the left-hand nucleus is substituted, provided that the compound wherein $R^1$ represents methyl, $R^2$, $R^3$ and W each represent a hydrogen atom is excluded.

The present invention, in another aspect thereof, provides an insecticidal or acaricidal composition which comprises as an active ingredient a compound of general formula (I).

DETAILED DESCRIPTION OF THE INVENTION

Compound

The compound according to the present invention are 4-acyloxyquinoliner derivative represented by the above-mentioned general formula (I).

$R^1$, $R^2$, $R^3$ and W have the following meanings.

In the compounds of formula (I), $R^1$ represents a hydrogen atom, a $C_1-C_{18}$ alkyl, $C_2-C_{18}$ alkenyl, $C_3-C_{10}$ cycloalkyl which may be optionally substituted, phenylloweralkyl, phenoxyloweralkyl, aryl group, a group $OR^4$, where $R^4$ represents a lower alkyl or aryl group, or a group

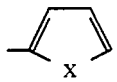

where X represents an oxygen or a sulphur atom.

A $C_1-C_{18}$ alkyl and $C_2-C_{10}$ alkenyl group may be a straight or branched chain. A $C_3-C_{10}$ cycloalkyl may be substituted by a halogen atom, a lower alkyl or lower alkenyl group.

An aryl group may be, for example, a phenyl group or a lower alkyl- and/or halogen-substituted phenyl, or a naphthyl, or a lower alkyl- and/or halogen-substituted naphthyl group.

The term "lower alkyl" is intended to mean a straight or branched chain alkyl group of from one to about four, preferable one to three, carbon atoms.

In the compounds of formula (I), $R^2$ represents a hydrogen atom, a lower alkyl group or a group $—COOR^5$, wherein $R^5$ represents a hydrogen atom or a lower alkyl group. The lower alkyl group is as defined above.

In the compounds of formula (I), $R^3$ represents a hydrogen atom, a $C_1-C_{10}$ alkyl or $C_2-C_{10}$ alkenyl group. A $C_1-C_{10}$ alkyl or $C_2-C_{10}$ alkenyl group may be a straight or branched chain.

In the compounds of formula (I), $R^1$ does not represent $OR^4$ when $R^2$ is a hydrogen atom and $R^3$ is methyl.

$R^2$ and $R^3$ together represent a group $-(CH_2)_{\overline{m}}$, wherein m is 3 or 4.

In the compounds of formula (I), W represents a hydrogen atom or 1 to 4 halogen atoms, such as fluorine, chlorine bromine and iodine, a lower alkyl or lower alkoxy group, which may be the same or different and with which the left-hand nucleus is substituted. That is, W represents not only one of the groups such as halogen atoms and a lower alkyl and lower alkoxy group but also two to four of them which are attached to the benzene ring moiety of the molecule.

The term "lower alkoxy" is intended to mean a straight or branched chain alkoxy group of from one to about four, preferably one to three, carbon atoms.

The compound wherein $R^1$ represents methyl, $R^2$, $R^3$ and W each represent a hydrogen atom is however excluded from the present invention.

Specific examples of the compounds of the present invention represented by the formula (I) include the following compounds:
4-acetoxy-2,3-dimethyl-6-fluoroquinoline,
4-acetoxy-2-ethyl-6-fluoro-3-methylquinoline,
4-cyclopropanecarbonyloxy-2-ethyl-6-fluoro-3-methylquinoline,
4-ethoxycarbonyloxy-2-ethyl-6-fluoro-3-methylquinoline, and
4-acetoxy-2-(cis-1-nonenyl)-3-methylquinoline.

Synthesis of the Compound

The compounds represented by the formula (I) can be synthesized by any appropriate methods with reference to the formation of bonds or the introduction of substituents.

For example, the compound represented by the formula (I) can be synthesized in accordance with well-known methods, for example, those described in (i) J. Chem. Soc. (C), 1970, 2426; (ii) Tetrahedron Lett., 1968, 4945; or (iii) Tetrahedron Lett., 1971, 4223, and outlined hereinafter. In the following description, the group $R^1$, $R^2$, $R^3$ and W are as previously definened for compounds of general formula (I).

A compound of general formula (I) may be prepared by reacting the compound of formula (II), with a compound of formula (III) or (IV) in the presence or absence of a base:

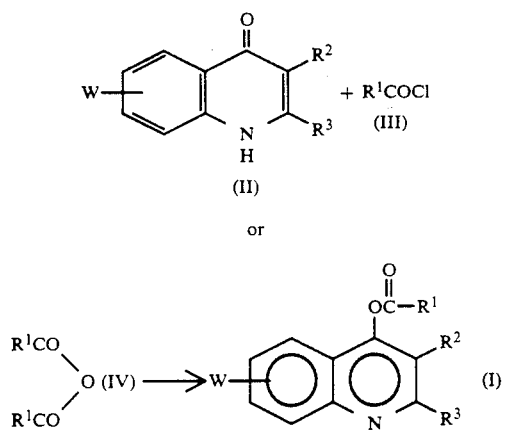

Examples of the base are organic amines such as triethylamine and pyridine, and inorganic alkalis such as sodium carbonate, potassium carbonate and sodium hydride. The compounds of formula (II) can be synthesized in accordance with well-known methods, for example those described in (i) J. Am. Chem. Soc., 70, 2402, (1948); (ii) Tetrahedron Lett., 27, 5323 (1986).

Use of Compound/Insecticidal and Acaricidal Composition

The compounds of formula (I) are effective for killing harmful insects, for example, Hemiptera such as aphids, plaxthoppers, leafhoppers, and bugs; Lepidoptera such as Tobacco Cutworm, and Diamondback Moth; Thripidae such as *Thrips palmi*; Coleoptera such as beatles and weevils; Diptera such as Housefly and mosquitoes; Blattaria such as cockroachs; Acarina such as *Tetranychus cinnabarinus* and *Dermatophgoides farinae*; Orthoptera.

The compound of formula (I), when used as an effective ingredient of an insecticide or acarticide, may be used directly as the raw material or generally is mixed with auxiliaries for preparations such as a solid carrier, a liquid carrier, a gas carrier, a surfactant or a dispersant or feed into any preparation forms such as an emulsion, a liquid agent, a hydration agent, a powder, a pellet, an oil agent, an aerosol, a flowable agent or a toxic feed.

As the solid carrier, there are mentioned, for example, talc, bentonite, clay, kaoline, diatomaceous earth, vermiculite, white carbon and calcium carbonate. The liquid carrier includes alcohols such as methanol, n-hexanol, ethylene glycol and cellosolve; ketones such as acetone, methyl ethyl ketone and cyclohexanone; aliphatic hydrocarbons such as kerosine and a lamp oil; aromatic hydrocarbons such as benzen, toluene, xylene and methylnaphthalene; halogenated hydrocarbons such as dichloroethane, trichloroethylene and carbon tetrachloride; ethers such as diethyl ether, dioxane and tetrahydrofuran; esters such as ethyl acetate; nitriles such as acetonitrile and isobutyronitrile; acid amides such as dimethylformamide and dimethylacetamide; plant oils such as soy bean oil and cotton seed oil; dimethylsulfoxide and water. As the gaseous carrier, there are mentioned, for example, LPG, flon gas, air, nitrogen, carbon dioxide gas and dimethyl ether.

As the surfactant or the dispersant for emulsification, dispersion, spreading or the like, there are used, for example, alkylsulfate esters, alkyl (or aryl) sulfonate salts, polyoxyalkylene alkyl (or aryl) ethers, polyalcohol esters, lignin sulfonate salts or the like.

Moreover, as the auxiliary for improving the properties of the preparation, there are used, for example, carboxymethylcellulose, gum arabic, polyethylene glycol, calcium stearate or the like.

The aforementioned carriers, surfactants, dispersants and auxiliaries are used alone or in combination thereof, if required.

The amount of active ingredients in the preparation is usually in the range of 1 to 75 parts by weight for the emulsion, 0.3-25 parts by weight for the powder, 1-90 parts by weight for the hydration agent, and 0.5-10 parts by weight for the particles.

These preparations are used directly or upon dilution. They can be also used in admixture with other insecticides, acaricides, bacteriocides, herbicides, plant growth controlling agents, fertilizers, soil conditioners, synergists or the like.

Some of the embodiments of the insecticides of the present invention include the following compounds as the active ingredients:
4-acetoxy-2,3-dimethyl-6-fluoroquinoline,
4-acetoxy-2-ethyl-6-fluoro-3-methylquinoline,
4-cyclopropanecarbonyloxy-2-ethyl-6-fluoro-3-methylquinoline,
4-ethoxycarbonyloxy-2-ethyl-6-fluoro-3-methylquinoline, and
4-acetoxy-2-(cis-1-nonenyl)-3-methylquinoline.

EXPERIMENTAL EXAMPLES

The present invention is further explained in detail with reference to the experimental examples. The present invention will not be limited to these illustrations.

EXAMPLE 1

4-acetoxy-2,3-dimethylquinoline (Compound No. 1)

A solution of 1.73 g of 2,3-dimethyl-4-quinolone in 25 ml of acetic anhydride was stirred at 130° C. for 8 hours. The solution was evaporated to remove the solvent under reduced pressure, and 30 ml of chloroform was added to the solution. The mixture was washed with an aqueous saturated sodium hydrogen carbonate solution and water and dried over sodium sulfate. The solvent was evaporated under reduced pressure, and the crude product thus obtained was purified by silica gel column chromatography (Wako Gel C-200) to give 1.87 g of 4-acetoxy-2,3-dimethylquinoline.

m.p.: 93°-94° C.

NMR (CDCl$_3$) δ: 2.24 (s,3H), 2.47 (s,3H), 2.69 (s,3H), 7.3-8.1 (m,4H).

EI-ms: 215 (M$^+$), 173.

EXAMPLE 2

4-cyclopropanecarbonyloxy-2-ethyl-6-fluoro-3-methylquinoline (Compound No. 2)

To a solution of 180 mg of sodium hydride in 10 ml of dimethylformamide was added 923 mg of 2-methyl-6-fluoro-3-methyl-4-quinolone on an ice bath, and the solution was stirred at room temperature for 15 min. After the solution was cooled on an ice bath, and 470 mg of cyclopropanecarbonyl chloride was added to the solution, and the mixture was stirred at room temperature for 4 hours. The mixture was poured into 20 ml of water. The solution was extracted with chloroform, and the chloroform solution was washed with water, dried over sodium sulfate. The solvent was evaporated under reduced pressure, and the crude product thus obtained was purified by silica gel column chromatography (Wako Gel C-200, n-hexane:ethyl acetate=7:1) to give 1.02 g of 4-cyclopropanecarbonyloxy-2-ethyl-6-fluoro-3-methylquinoline.

m.p.: 86°–87° C.,

NMR (CDCl$_3$) δ: 1.0~1.5 (m,6H), 1.6~2.2 (m, 2H), 2.28 (s,3H), 3.00 (q, 2H, J=7.5 Hz), 7.1~7.5 (m,2H), 8.03 (dd, 1H, J=9 Hz, 5 Hz). ir (KBr) 2900, 2760, 1600, 1560, 1200 cm$^{-1}$.

EI-MS: 273 (M+), 205.

Compound No. 3–compound No. 65 were synthesized below in similar manners as in the above described preparation examples.

| Compound No. | Compound | Spectral data | m.p. |
|---|---|---|---|
| 3 | 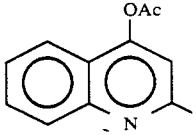 (Ac: —COCH3) | NMR(CDCl$_3$) δ: 2.44(s, 3H), 2.72(s, 3H), 7.12(s, 1H), 7.3~8.1(m, 4H). ir(neat) 1760, 1620, 1600, 1190 cm$^{-1}$ | oil |
| 4 | 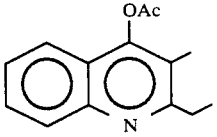 | NMR(CDCl$_3$) δ: 1.36(t, 3H, J=8Hz), 2.25(s, 3H), 2.44(s, 3H), 2.99(q, 2H, J=8Hz), 7.3~8.1(m, 4H). ir(KBr)2950, 1760, 1620, 1600, 1550, 1200 cm$^{-1}$ EI-ms 229(M+), 187, 186, | 66~67° C. |
| 5 | 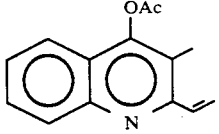 | NMR(CDCl$_3$) δ: 2.28(s, 3H), 2.44(s, 3H), 5.58(dd, 1H, J=12Hz, J=2Hz), 6.44(dd, 1H, J=19Hz, J=2Hz), 7.11(dd, 1H, J=19Hz, J=12Hz), 7.4~8.1(m, 4H). EI-ms 227(M+), 185, 184 | 55~56° C. |
| 6 | 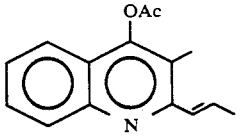 | NMR(CDCl$_3$) δ: 1.97(d, 3H, J=6Hz), 2.24(s, 3H), 2.40(s, 3H), 6.72(d, 1H, J=15Hz), 6.8~7.3(m, 1H), 7.3~8.1(m, 4H). EI-ms 241(M+), 199, 198, 184 | 142~143° C. |
| 7 | 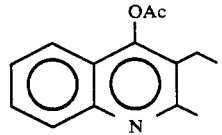 | NMR(CDCl$_3$) δ: 1.19(t, 3H, J=7.5Hz), 2.46(s, 3H), 2.74(s, 3H), 2.70(q, 2H, J=7.5Hz), 7.3~8.1(m, 4H). EI-ms 229(M+) | 40~41° C. |
| 8 | 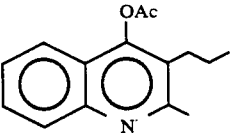 | NMR(CDCl$_3$) δ: 1.01(t, 3H, J=8Hz), 1.40~1.80(m, 2H), 2.47(s, 3H), 2.74(s, 3H), 2.50~2.70(m, 2H), 7.30~7.70(m, 3H), 7.90~8.10(m, 1H). ir(neat)2950, 1760, 1620, 1600, 1190 cm$^{-1}$ EI-ms 243(M+), 201 | oil |
| 9 | 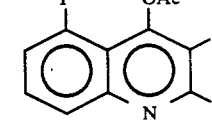 | NMR(CDCl$_3$) δ: 2.22(s, 3H), 2.39(s, 3H), 2.65(s, 3H), 7.10(ddd, 1H, J=12Hz, J=8Hz, J=1Hz), 7.52(dt, 1H, J=6Hz, J=8Hz), 7.88(d, 1H, J=8Hz). ir(KBr)3000, 1760, 1620, 1600, 1560, 1200 cm$^{-1}$ EI-ms (233(M+), 191 | 111~112° C. |
| 10 | 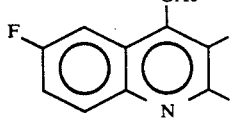 | NMR(CDCl$_3$) δ: 2.22(s, 3H), 2.47(s, 3H), 2.67(s, 3H), 7.13~7.48(m, 2H), 7.93(dd, 1H, J=9Hz, J=5Hz). EI-ms 233(M+), 191 ir(KBr)3000, 1750, 1600, 1560, 1200 cm$^{-1}$. | 107~108° C. |

-continued

| Compound No. | Compound | Spectral data | m.p. |
|---|---|---|---|
| 11 | 7-fluoro-2,3-dimethyl-4-acetoxyquinoline | NMR(CDCl₃) δ: 2.20(s, 3H), 2.46(s, 3H), 2.67(s, 3H),<br>7.26(dt, 1H, J=9Hz, J=2.6Hz),<br>7.64(dd, 1H, J=10Hz, J=2.6Hz),<br>7.69(dd, 1H, J=9Hz, J=6Hz).<br>ir(KBr)2920, 1760, 1620, 1560, 1500, 1200 cm⁻¹<br>EI-ms 233(M⁺), 191 | 105~106° C. |
| 12 | 8-fluoro-2,3-dimethyl-4-acetoxyquinoline | NMR(CDCl₃) δ: 2.24(s, 3H), 2.47(s, 3H),<br>2.74(s, 3H), 7.1~7.5(m, 3H).<br>ir(KBr)2900, 1760, 1600, 1200 cm⁻¹<br>EI-ms 233(M⁺), 191 | 122~123° C. |
| 13 | 6,8-difluoro-2,3-dimethyl-4-acetoxyquinoline | NMR(CDCl₃) δ: 2.23(s, 3H), 2.46(s, 3H),<br>2.71(S, 3H), 6.97~7.27(m, 2H).<br>EI-ms 251(M⁺), 209, 180 | 116~117° C. |
| 14 | 4-propionyloxy-2,3-dimethylquinoline (OCCH₂CH₃) | NMR(CDCl₃) δ: 1.36(t, 3H, J=7.5Hz),<br>2.21(s, 3H), 2.69(s, 3H),<br>2.78(q, 2H, J=7.5Hz), 7.3~8.1(m, 4H).<br>ir(KBr)2900, 1750, 1620, 1600, 1140 cm⁻¹.<br>EI-ms 229(M⁺), 173 | 76~77° C. |
| 15 | 4-decanoyloxy-2,3-dimethylquinoline (OC(CH₂)₈CH₃) | NMR(CDCl₃) δ: 0.77~1.03(m, 3H),<br>1.10~1.60(m, 14H), 1.70~2.10(m, 2H),<br>2.21(s, 3H), 2.68(s, 3H),<br>2.74(t, 2H, J=7.5Hz), 7.3~8.1(m, 4H).<br>EI-ms 327(M⁺), 174, 173<br>ir(KBr)2900, 2850, 1750, 1620, 1600,<br>1140 cm⁻¹. | 52~53° C. |
| 16 | 4-benzoyloxy-2,3-dimethylquinoline | NMR(CDCl₃) δ: 2.28(s, 3H), 2.72(s, 3H),<br>7.2~8.4(m, 9H).<br>EI-ms 277(M⁺)<br>ir (KBr) 3000, 1720, 1620, 1600, 1240 cm⁻¹. | 163~164° C. |
| 17 | 4-acetoxy-3-ethoxycarbonyl-2-methylquinoline | NMR(CDCl₃) δ: 1.40(t, 3H, J=7Hz),<br>2.42(s, 3H), 2.81(s, 3H),<br>4.40(q, 2H, J=7Hz), 7.3~8.1(m, 4H).<br>EI-ms 273(M⁺), 231, 186 | 92~93° C. |
| 18 | 4-acetoxy-1,2,3,4-tetrahydroacridine | NMR(CDCl₃) δ: 1.60~2.10(m, 4H),<br>2.42(s, 3H), 2.60~2.83(m, 2H),<br>2.97~3.20(m, 2H), 7.2~8.1(m, 4H).<br>EI-ms 241(M⁺), 199, 198 | 102~103° C. |
| 19 | 4-acetoxy-3-methyl-2-propylquinoline | NMR(CDCl₃) δ: 1.05(t, 3H, J=8Hz),<br>1.60~2.10(m, 2H), 2.26(s, 3H),<br>2.46(s, 3H), 2.95(t, 2H, J=8Hz),<br>7.30~7.75(m, 3H), 7.90~8.10(m, 1H).<br>EI-ms 243(M⁺), 200, 173 | 98~99° C. |

| Compound No. | Compound | Spectral data | m.p. |
|---|---|---|---|
| 20 | 6-F, 2-ethyl, 3-methyl, 4-OAc quinoline | NMR(CDCl₃) δ: 1.34(t, 3H, J=8Hz), 2.23(s, 3H)2.44(s, 3H), 2.96(q, 2H, J=8Hz), 7.10~7.50(m, 2H), 8.04(dd, 1H, J=9Hz, J=5Hz). ir(KBr) 2970, 1760, 1610, 1210 cm⁻¹ EI-ms 247(M⁺), 205, 204 | 111~112° C. |
| 21 | 6-Cl, 2,3-dimethyl, 4-OAc quinoline | NMR(CDCl₃) δ: 2.19(s, 3H), 2.45(s, 3H), 2.65(s, 3H), 7.40~7.65(m, 2H), 7.89(d, 1H, J=8.8Hz). ir(KBr) 1760, 1600, 1480, 1200 cm⁻¹ EI-ms 249(M⁺), 207 | 112~113° C. |
| 22 | 6-Cl, 2-ethyl, 3-methyl, 4-OAc quinoline | NMR(CDCl₃) δ: 1.35(t, 3H, J=7.5Hz), 2.25(s, 3H), 2.48(s, 3H), 2.98(q, 2H, J=7.5Hz), 7.40~7.70(m, 2H), 7.95(d, 1H, J=8.8Hz). ir(KBr) 2960, 1760, 1600, 1480, 1200 cm⁻¹ EI-ms 263(M⁺), 221 | 106~107° C. |
| 23 | 4-OC(=O)(CH₂)₂CH₃, 2,3-dimethyl quinoline | NMR(CDCl₃) δ: 1.13(t, 3H, J=8Hz), 1.92(m, 2H), 2.25(s, 3H), 2.72(s, 3H), 2.77(t, 2H), 7.4~8.1(m, 4H), EI-ms 243(M⁺), 173, 144 | 78~80° C. |
| 24 | 4-OC(=O)CH(CH₃)₂, 2,3-dimethyl quinoline | δ: 1.50(d, 6H, J=7Hz), 2.52(s, 3H), 3.10(s, 3H), 3.11(m, 1H), 7.7~8.8(m, 4H), EI-ms 243(M⁺), 173, 144 | 130° C. |
| 25 | 4-OC(=O)CH=CHCH₃, 2,3-dimethyl quinoline | δ: 2.06(dd, 3H, J=6.9, 1.8Hz), 2.26(s, 3H), 2.73(s, 3H), 6.23(m, 1H), 7.36(m, 1H), 7.4~8.1(m, 4H) EI-ms 241(M⁺), 173, 144 | 133~135° C. |
| 26 | 4-OC(=O)OCH₂CH₃, 2,3-dimethyl quinoline | δ: 1.44(t, 3H, J=7.2Hz), 2.32(s, 3H), 2.73(s, 3H), 4.39(q, 2H, J=7.2Hz), 7.4~8.1(m, 4H), EI-ms 245(M⁺), 201, 173, 144 | 79~81° C. |
| 27 | 4-OC(=O)CH₂Ph, 2,3-dimethyl quinoline | δ: 2.12(s, 3H), 2.69(s, 3H), 4.05(s, 2H), 7.3~8.0(m, 9H), EI-ms 291(M⁺), 174, 144 | 104~106° C. |
| 28 | 4-OC(=O)cyclohexyl, 2,3-dimethyl quinoline | δ: 1.29~1.49(m, 3H), 1.68~1.94(m, 5H), 2.23(s, 3H), 2.23~2.25(m, 2H), 2.72(s, 3H), 2.75~2.83(m, 1H), 7.44~8.02(m, 4H), EI-ms 283(M⁺), 173, 144 | 87~88° C. |

-continued

| Compound No. | Compound | Spectral data | m.p. |
|---|---|---|---|
| 29 | (2,3-dimethylquinolin-4-yl adamantane-1-carboxylate) | δ: 1.71~2.30(m, 15H), 2.22(s, 3H), 2.72(s, 3H), 7.44~8.02(m, 4H), EI-ms 335(M⁺), 173, 144 | 174~178° C. |
| 30 | OC(=O)(CH₂)₇CH=CH(CH₂)₇CH₃ on 2,3-dimethylquinolin-4-yl | δ: 0.88(t, 3H, J=6.8Hz), 1.18~1.54(m, 20H), 1.87(quintet, 2H, J=7.6Hz), 1.92~2.10(m, 4H), 2.24(s, 3H), 2.72(s, 3H), 5.31~5.42(m, 2H), 7.45~8.02(m, 4H) EI-ms 437(M⁺), 265, 173, 144 | oil |
| 31 | OCOCH₃ on 2,3-dimethylquinolin-4-yl | δ: 2.32(s, 3H), 2.74(s, 3H), 3.99(s, 3H), 7.5~8.0(m, 4H) EI-ms 231(M⁺), 172, 144 | 77~79° C. |
| 32 | 4-OAc-3-methyl-2-(non-1-enyl)quinoline | NMR(CDCl₃) δ: 0.84(t, 3H, J=6Hz), 1.1~1.6(m, 10H), 2.2~2.7(m, 2H), 2.26(s, 3H), 2.49(s, 3H), 6.02(dt, 1H, J=12Hz, 7Hz), 6.61(d, 1H, J=12Hz), 7.3~8.1(m, 4H) | oil |
| 33 | OC(=O)(CH₂)₁₄CH₃ on 2,3-dimethylquinolin-4-yl | δ: 0.88(m, 3H), 1.2~1.4(m, 26H), 1.45~1.54(m, 2H), 1.84~1.92(m, 2H), 2.25(s, 3H), 2.73(s, 3H), 2.78(t, 2H, J=7.6Hz), 7.4~8.0(m, 4) EI-ms 411(M⁺), 239, 173, 144 | 69~71° C. |
| 34 | OCCH₂CH(CH₃)₂ on 2,3-dimethylquinolin-4-yl | δ: 1.14(d, 6H, 6.7Hz), 2.25(s, 3H), 2.32~2.39(m, 1H), 2.67(d, 2H, J=6.9Hz), 2.72(s, 3H), 7.45~8.02(m, 4H) EI-ms 257(M⁺), 173, 144 | 66~67° C. |
| 35 | OCC(CH₃)₃ on 2,3-dimethylquinolin-4-yl | δ: 1.53(s, 9H), 2.24(s, 3H), 2.73(s, 3H), 7.45~8.02(m, 4H) EI-ms 257(M⁺), 173, 144 | 141~142° C. |
| 36 | O-C(=O)-cyclopropyl on 2,3-dimethylquinolin-4-yl | δ: 1.13~1.19(m, 2H), 1.28~1.32(m, 2H), 2.03~2.10(m, 1H), 2.26(s, 3H), 2.72(s, 3H), 7.46~8.02(m, 4H) EI-ms 241(M⁺), 173, 144 | 87~88° C. |

-continued

| Compound No. | Compound | Spectral data | m.p. |
|---|---|---|---|
| 37 | 4-OCOCH(CH₃)₂, 2,3-dimethylquinoline | δ: 1.43(d, 6H, J=6.2Hz), 2.32(s, 3H), 2.74(s, 3H), 5.03(m, 1H), 7.48~8.03(m, 4H)<br>EI-ms 259(M⁺), 200, 173, 144 | 71~72° C. |
| 38 | 4-OCO(CH₂)₃CH₃, 2,3-dimethylquinoline | δ: 0.99(t, 3H, J=7.3Hz), 1.42~1.53(m, 2H), 1.74~1.81(m, 2H), 2.32(s, 3H), 2.73(s, 3H), 4.33(t, 2H; J=6.7Hz), 7.49~8.03(m, 4H)<br>EI-ms 273(M⁺), 200, 173, 144 | 42~44° C. |
| 39 | 4-OCOPh, 2,3-dimethylquinoline | δ: 2.40(s, 3H), 2.75(s, 3H), 7.24~8.06(m, 9H)<br>EI-ms 293(M⁺), 173, 156 | 87~89° C. |
| 40 | 4-OAc, 3-methyl, 2-butylquinoline | NMR(CDCl₃) δ: 0.96(t, 3H, J=6.6Hz), 1.3~2.0(m, 4H), 2.26(s, 3H), 2.46(s, 3H), 2.86~3.10(m, 2H), 7.3~7.8(m, 3H), 8.01(d, 1H, J=8Hz)<br>EI-ms 257(M⁺), 215 | 74~75° C. |
| 41 | 4-OAc, 3-methyl, 2-pentylquinoline | NMR(CDCl₃) δ: 0.75~1.05(m, 3H), 1.25~1.95(m, 6H), 2.28(s, 3H), 2.49(s, 3H), 2.8~3.1(m, 2H), 7.3~7.7(m, 3H), 8.02(d, 1H, J=8Hz)<br>EI-ms 271(M⁺), 215 | 64~65° C. |
| 42 | 4-OAc, 3-methyl, 2-hexylquinoline | NMR(CDCl₃) δ: 0.87(t, 3H, J=6Hz), 1.1~2.0(m, 8H), 2.26(s, 3H), 2.46(s, 3H), 2.97(dd, 2H, J=9Hz, J=7Hz), 7.2~7.7(m, 3H), 8.00(d, 1H, J=8Hz)<br>EI-ms 285(M⁺), 242, 215 | 55~56° C. |
| 43 | 6-F, 4-OAc, 3-methyl, 2-hexylquinoline | NMR(CDCl₃) δ: 0.87(t, 3H, J=6Hz), 1.1~1.9(m, 8H), 2.24(s, 3H), 2.46(s, 3H), 2.94(dd, 2H, J=9Hz, J=7Hz), 7.1~7.5 (m, 2H), 7.99(dd, 1H, J=9.0Hz, J=5.3Hz)<br>EI-ms 303(M⁺) | 66~67° C. |
| 44 | 4-OAc, 3-methyl, 2-hexylquinoline | NMR(CDCl₃) δ: 0.86(t, 3H, J=6Hz), 1.0~1.45(m, 8H), 1.5~1.9(m, 2H), 2.43(s, 3H), 2.95(dd, 2H, J=9Hz, J=7Hz), 7.16(s, 1H), 7.2~8.1(m, 4H)<br>EI-ms 285(M⁺), 242, 201 | oil |
| 45 | 4-OAc, 3-methyl, 2-heptylquinoline | NMR(CDCl₃) δ: 0.86(t, 3H, J=6Hz), 1.1~1.5(m, 8H), 1.6~1.9(m, 2H), 2.25(s, 3H), 2.45(s, 3H), 2.96(dd, 2H, J=9Hz, J=7Hz), 7.3~7.8(m, 3H), 8.00(d, 1H, J=8Hz)<br>EI-ms 299(M⁺), 256, 215 | 57~58° C. |

| Compound No. | Compound | Spectral data | m.p. |
|---|---|---|---|
| 46 | CH₃O-[quinoline with OAc, 2,3-dimethyl] | NMR(CDCl₃) δ: 2.18(s, 3H), 2.44(s, 3H), 2.64(s, 3H), 3.85(s, 3H), 6.88(d, 1H, J=2.6Hz), 7.25(dd, 1H, J=9.2Hz, J=2.6Hz), 7.89(d, 1H, J=9.2Hz) EI-ms 245(M⁺), 203 | 106~107° C. |
| 47 | Ethyl-[quinoline with OAc, 2,3-dimethyl] | NMR(CDCl₃) δ: 1.27(t, 3H, J=7.6Hz), 2.20(s, 3H), 2.46(s, 3H), 2.66(s, 3H), 2.77(q, 2H, J=7.6Hz), 7.33-7.53(m, 2H), 7.91(d, 1H, J=8.4Hz) EI-ms 243(M⁺), 201 | 87~88° C. |
| 48 | 8-Ethyl-[quinoline with OAc, 2,3-dimethyl] | NMR(CDCl₃) δ: 1.31(t, 3H, J=7.5Hz), 2.17(s, 3H), 2.41(s, 3H), 2.65(s, 3H), 3.23(q, 2H, J=7.5Hz), 7.23~7.53(m, 3H), EI-ms 243(M⁺) | 73~74° C. |
| 49 | Propyl-[quinoline with OAc, 2,3-dimethyl] | NMR(CDCl₃) δ: 0.91(t, 3H, J=6.2Hz), 1.20~1.84(m, 4H), 2.20(s, 3H), 2.46(s, 3H), 2.66(s, 3H), 2.7~2.9(m, 2H), 7.3-7.5(m, 2H), 7.89(d, 1H, J=8Hz) EI-ms 271(M⁺), 229 | 80~81° C. |
| 50 | Quinoline-4-yl thiophene-2-carboxylate | NMR(CDCl₃) δ: 2.32(s, 3H), 2.75(s, 3H), 7.25(dd, 1H, J=5.1Hz, J=3.7Hz), 7.3~8.2(m, 6H) EI-ms 283(M⁺) | 153~154° C. |
| 51 | Quinoline-4-yl furan-2-carboxylate | NMR(CDCl₃) δ: 2.31(s, 3H), 2.76(s, 3H), 6.67(q, 1H, J=1.8Hz), 7.2~7.8(m, 5H), 8.06(d, 1H, J=8Hz) EI-ms 267(M⁺), 172 | 115~116° C. |
| 52 | 2-Octyl-[quinoline with OAc] | NMR(CDCl₃) δ: 0.85(t, 3H, J=6Hz), 1.1~1.5(m, 12H), 1.6~1.9(m, 2H), 2.42(s, 3H), 2.95(dd, 2H, J=9Hz, J=7Hz), 7.14(s, 1H), 7.3~8.1(m, 4H), EI-ms 313(M⁺), 270, 201 | oil |
| 53 | 2-Octyl-3-methyl-[quinoline with OAc] | NMR(CDCl₃) δ: 0.85(t, 3H, J=6Hz), 1.1~1.5(m, 12H), 1.6~1.9(m, 2H), 2.23(s, 3H), 2.43(s, 3H), 2.97(dd, 2H, J=9Hz, J=7Hz), 7.3~7.7(m, 3H), 7.98(d, 1H, J=8Hz) EI-ms 327(M⁺), 284, 215 | 52~53° C. |
| 54 | 6-Fluoro-2-octyl-3-methyl-[quinoline with OAc] | NMR(CDCl₃) δ: 0.88(t, 3H, J=6Hz), 1.1~1.5(m, 12H), 1.6~2.0(m, 2H), 2.27(s, 3H), 2.49(s, 3H), 2.96(dd, 2H, J=9Hz, J=7Hz), 7.1~7.5(m, 2H), 8.02(dd, 1H, J=5Hz, J=9Hz) EI-ms 346(M⁺) | 78~79° C. |

-continued

| Compound No. | Compound | Spectral data | m.p. |
|---|---|---|---|
| 55 | 6-F, 3-methyl, 2-octyl quinoline with 4-O-C(=O)-cyclopropyl | NMR(CDCl₃) δ: 0.89(t, 3H, J=5Hz), 1.0~2.1(m, 13H), 2.27(s, 3H), 2.95(dd, 2H, J=8Hz, 7Hz), 7.1~7.5(m, 2H), 7.96(dd, 1H, J=9Hz, J=5Hz) EI-ms 330(M⁺), 259 | 50~51° C. |
| 56 | 6-F, 3-methyl, 2-ethyl quinoline with 4-OC(=O)OCH₂CH₃ | NMR(CDCl₃) δ: 1.38(t, 3H, J=7.4Hz), 1.44(t, 3H, J=7.1Hz), 2.33(s, 3H), 3.01(q, 2H, J=7.4Hz), 4.39(q, 2H, J=7.1Hz), 7.1~7.5(m, 2H), 8.03(dd, 1H, J=10.0Hz, 5.2Hz) EI-ms 277(M⁺), 205 | 64~65° C. |
| 57 | 6-propyl, 3-methyl, 2-ethyl quinoline with 4-OC(=O)-cyclopropyl | NMR(CDCl₃) δ: 0.93(t, 3H, J=6Hz), 1.1~2.2(m, 9H), 2.21(s, 3H), 2.67(s, 3H), 2.7~2.9(m, 2H), 7.3-7.5(m, 2H), 7.89(d, 1H, J=10Hz) EI-ms 297(M⁺), 229 | 83~84° C. |
| 58 | 6-F, 3-methyl, 2-ethyl quinoline with 4-OCOCH₃ | NMR(CDCl₃) δ: 1.35(t, 3H, J=7.5Hz), 2.31(s, 3H), 2.98(q, 2H, J=7.5Hz), 3.95(s, 3H), 7.1~7.5(m, 2H), 7.99(dd, 1H, J=10Hz, 5Hz) EI-ms 263(M⁺), 204 | 67~68° C. |
| 59 | 6-F, 3-methyl, 2-ethyl quinoline with 4-OCOCH(CH₃)₂ | NMR(CDCl₃) δ: 1.38(t, 3H, J=7.7Hz), 1.39(s, 3H), 1.46(s, 3H), 2.33(s, 3H), 4.8~5.2(m, 1H), 7.2~7.5(m, 2H), 8.03(dd, 1H, J=10.1Hz, 5.3Hz) EI-ms 292(M⁺), 291(M⁺), 205 | 52~53° C. |
| 60 | 6-F, 3-methyl, 2-ethyl quinoline with 4-OCCH₂CH₃ | NMR(CDCl₃) δ: 1.40(t, 3H, J=7.5Hz), 2.27(s, 3H), 2.6~3.2(m, 4H), 7.1~7.5(m, 2H), 7.98(dd, 1H, J=9Hz, 5Hz) EI-ms 261(M⁺), 205 | 114~115° C. |
| 61 | 6-F, 3-methyl, 2-ethyl quinoline with 4-OCCH₂CH(CH₃)₂ | NMR(CDCl₃) δ: 1.11(s, 3H), 1.18(s, 3H), 1.37(t, 3H, J=7.5Hz), 2.1~2.5(m, 1H), 2.27(s, 3H), 2.66(d, 2H, J=6.6Hz), 3.01(q, 2H, J=7.5Hz), 7.1~7.5(m, 2H), 8.03(dd, 1H, J=9Hz, 5.5Hz) EI-ms 289(M⁺), 205 | 73-74° C. |
| 62 | 6-F, 3-methyl, 2-ethyl quinoline with 4-OCCH₂C(CH₃)₃ | NMR(CDCl₃) δ: 1.22(s, 9H), 1.37(t, 3H, J=7.5Hz), 2.28(s, 3H), 2.69(s, 3H), 3.01(q, 2H, J=7.5Hz), 7.1~7.5(m, 2H), 8.02(dd, 1H, J=9.0Hz, 5.5Hz) EI-ms 303(M⁺), 205 | 82-83° C. |

| Compound No. | Compound | Spectral data | m.p. |
|---|---|---|---|
| 63 | (F-quinoline with O-C(=O)-cyclohexyl, methyl, ethyl substituents) | NMR(CDCl₃) δ: 1.37(t, 3H, J=7.5Hz), 1.4~2.4(m, 10H), 2.25(s, 3H), 2.5-2.9(m, 1H), 3.00(q, 2H, J=7.5Hz), 7.1-7.5(m, 2H), 8.02(dd, 1H, J=9.2Hz, 5.1Hz) EI-ms 315(M⁺), 232, 205 | 96~97° C. |
| 64 | (F-quinoline with O-C(=O)-cyclobutyl, methyl, ethyl substituents) | NMR(CDCl₃) δ: 1.37(t, 3H, J=7.5Hz), 1.7~2.2(m, 3H), 2.26(s, 3H), 2.23~2.7(m, 3H), 3.00(q, 2H, J=7.5Hz), 3.57(q, 1H, J=8.6Hz), 7.1~7.5(m, 2H), 8.02(dd, 1H, J=9.1Hz, 5.3Hz) EI-ms 287(M⁺), 232, 205 | 85~86° C. |
| 65 | (F-quinoline with O-C(=O)-C(CH₃)₂CH₂CH=C(CH₃)₂ substituent) | NMR(CDCl₃) δ: 1.29(s, 3H), 1.34(t, 3H, J=7.7Hz), 1.38(s, 3H), 1.7~1.9(m, 7H), 2.1~2.4(m, 1H), 2.26(s, 3H), 2.98(q, 2H, J=7.7Hz), 4.9~5.4(m, 1H), 7.1~7.5(m, 2H), 7.8~8.1(m, 1H) EI-ms 355(M⁺), 205 | 87~88° C. |

PREPARATION EXAMPLE 1

Emulsion

A 10 parts by weight amount of polyoxyethylenealkyl allyl ether was added to the mixture of 20 parts by weight of the compound of the present invention, 20 parts by weight of N,N-dimethylformamide and 50 parts by weight of xylene, and the mixture was uniformly mixed and dissolved to give an emulsion.

PREPARATION EXAMPLE 2

Hydration Agent

Twenty five parts by weight of the compound of the present invention, 30 parts by weight of clay, 35 parts by weight of diatomaceous earth, 3 parts by weight of calcium lignin sulfate and 7 parts by weight amount of polyoxyethylenealkyl allyl ether were uniformly mixed and ground to give a hydration agent.

PREPARATION EXAMPLE 3

Powder

Two parts by weight of the compound of the present invention, 60 parts by weight of clay, 37 parts by weight of talc and 1 part by weight of calcium stearate were mixed uniformly to give a powder.

PREPARATION EXAMPLE 4

Pellet

Five parts by weight of the compound of the present invention, 40 parts by weight of bentonite, 53 parts by weight of talc and 2 parts by weight of calcium lignin sulfate were milled and mixed. The mixture was kneaded sufficiently with the addition of water before granulation and drying to give pellets.

TEST EXAMPLE 1

Test of Effectiveness of the Preparation on the Larva of Tobacco Cutworm

A preparation was prepared in accordance with Preparation Example 1, and 10 third or forth instar larvae of Tabacco Cut worm were dipped into the preparation liquid which had been diluted to 1000 ppm with water containing a surfactant (0.01%) for 10 seconds. The larvae were released to a plastic cup having a diameter of 9 cm into which piece of cabbage leaf (5 cm×5 cm), and the cup was left in an thermostat at 25° C. The survival number and mortality of the worms were counted after two days to obtain the mortality rate. The result is shown in Table 1.

Mortality (%)=(number of dead insects/released insects)×100

TABLE 1

| Compound No. | Mortality (%) |
|---|---|
| 2 | 100 |
| 4 | 100 |
| 9 | 100 |
| 10 | 100 |
| 14 | 90 |
| 15 | 100 |
| 20 | 100 |
| 21 | 100 |
| 22 | 100 |
| 23 | 70 |
| 26 | 100 |
| 28 | 100 |
| 31 | 100 |
| 34 | 100 |
| 36 | 90 |
| 37 | 100 |
| 38 | 100 |
| 47 | 90 |
| 56 | 100 |

TABLE 1-continued

| Compound No. | Mortality (%) |
| --- | --- |
| 57 | 100 |
| 58 | 100 |
| 59 | 100 |
| 60 | 100 |
| 61 | 100 |
| 62 | 100 |
| 63 | 100 |
| 64 | 100 |

TEST EXAMPLE 2

Test of Effectiveness of the Preparation on *Myzus persicae*

A preparation was prepared in accordance with Preparation Example 1, and a cabbage leaf piece on which 10 apterous viviparae of the aphid had been inoculated was dipped into the preparation liquid which had been diluted to 1000 ppm with water containing a surfactant (0.01%) for 10 seconds. After air drying, the leaf was placed in a plastic cup having a diameter of 9 cm and left in an thermostat at 25° C. The survival number and mortality of the worms were counted after one day to obtain the mortality. The result is shown in Table 2.

Mortality (%)=(number of dead insects/released insects)×100

TABLE 2

| Compound No. | Mortality (%) |
| --- | --- |
| 1 | 100 |
| 7 | 100 |
| 9 | 100 |
| 10 | 100 |
| 11 | 100 |
| 12 | 90 |
| 14 | 100 |
| 15 | 100 |
| 18 | 100 |
| 21 | 100 |
| 23 | 100 |
| 24 | 100 |
| 25 | 100 |
| 26 | 100 |
| 28 | 100 |
| 30 | 100 |
| 31 | 100 |
| 32 | 100 |
| 34 | 100 |
| 36 | 100 |
| 37 | 100 |
| 38 | 100 |
| 40 | 100 |
| 41 | 100 |
| 44 | 100 |
| 45 | 100 |
| 47 | 100 |
| 49 | 100 |
| 52 | 100 |
| 53 | 100 |
| 55 | 100 |
| 57 | 100 |

TEST EXAMPLE 3

Test of Effectiveness of the Preparation on *Tetranychus cinnabarinus* (Organic Phosphate Resistant)

A preparation was prepared in accordance with Preparation Example 1 and diluted to 1000 ppm with water containing a surfactant (0.01%). Ten of adult males of the mites were placed on a first leaf of kidney bean which had grown in a plastics pot having a diameter of 9 cm. After 24 hours, ten ml of the solution was sprayed on the leaf, and the pot was left in a thermostat at 25° C. The survival number and mortality of the worms were counted after two days to obtain the mortality rate. The result is shown in Table 3.

Mortality (%)=(number of dead mites/released mites)×100

TABLE 3

| Compound No. | Mortality (%) |
| --- | --- |
| 4 | 100 |
| 7 | 100 |
| 8 | 100 |
| 9 | 100 |
| 11 | 100 |
| 14 | 100 |
| 34 | 100 |
| 37 | 100 |
| 36 | 100 |
| 38 | 100 |
| 45 | 100 |
| 52 | 100 |
| 53 | 100 |

What is claimed is:

1. A 4-acyloxyquinoline derivative represented by the formula (I):

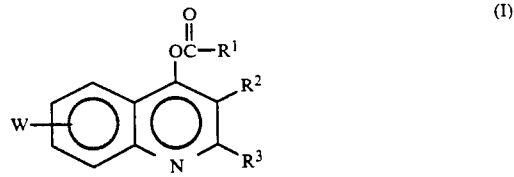

wherein

R$^1$ represents (1) hydrogen, (2) C$_1$–C$_{18}$ alkyl, (3) C$_3$–C$_{10}$ cycloalkyl which is unsubstituted or is substituted by halogen, lower alkyl, or lower alkenyl, (4) phenylloweralkyl, (5) phenoxyloweralkyl, (6) phenyl which is unsubstituted or is substituted by at least one of lower alkyl and halogen, (7) naphthyl which is unsubstituted or is substituted by at least one of lower alkyl and halogen, (8) OR$^4$ where R$^4$ represents (a) lower alkyl, (b) phenyl which is unsubstituted or is substituted by at least one of lower alkyl and halogen or (c) naphthyl which is unsubstituted or is substituted by at least one of lower alkyl and halogen, or (9) a group

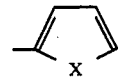

where X is is oxygen or sulphur,

R$^2$ represents (1) hydrogen, (2) lower alkyl or (3) —COOR$^5$ where R$^5$ is hydrogen or lower alkyl, R$^3$ represents (1) hydrogen or (2) C$_1$–C$_{10}$ alkyl, provided that R$^1$ does not represent OR$^4$ when R$^2$ is hydrogen and R$^3$ is methyl, and W represents one to four groups selected from (1) hydrogen, (2) halogen, (3) lower alkyl and (4) lower alkoxy, said substituent groups being the same or different, provided that the compound wherein R$^1$ is methyl and R$^2$, R$^3$ and W each are hydrogen is excluded.

2. 4-acetoxy-2,3-dimethyl-6-fluoroquinoline.

3. 4-acetoxy-2-ethyl-6-fluoro-3-methylquinoline.

4. 4-cyclopropanecarbonyloxy-2-ethyl-6-fluoro-3-methylquinoline.

5. 4-ethoxycarbonyloxy-2-ethyl-6-fluoro-3-methylquinoline.

6. An insecticidal or acaricidal composition which comprises as an active ingredient a compound of formula (I) as defined in claim 1 and a carrier therefor.

7. An insecticidal or acaricidal composition as claimed in claim 6, wherein the compound formula (I) is selected from the group consisting of:
4-acetoxy-2,3-dimethyl-6-fluoroquinoline,
4-acetoxy-2-ethyl-6-fluoro-3-methylquinoline,
4-cyclopropanecarbonyloxy-2-ethyl-6-fluoro-3-methylquinoline, and
4-ethoxycarbonyloxy-2-ethyl-6-fluoro-3-methylquinoline.

* * * * *